US008382657B1

(12) United States Patent
Bodor et al.

(10) Patent No.: US 8,382,657 B1
(45) Date of Patent: Feb. 26, 2013

(54) ENDOSCOPE TESTING DEVICE AND METHOD OF USING SAME

(75) Inventors: Zoltan A. Bodor, Plantation, FL (US); Matthew T. Goodale, Davie, FL (US); Oscar Jerome Williams, Miramar, FL (US); Marius Todor, Lake Worth, FL (US); Shusheng Ye, Davie, FL (US); Jurgen Zobel, Pembroke Pines, AL (US)

(73) Assignee: Integrated Medical Systems International, Inc, Birmingham, AL (US)

( * ) Notice: Subject to any disclaimer, the term of this patent is extended or adjusted under 35 U.S.C. 154(b) by 779 days.

(21) Appl. No.: 12/573,252

(22) Filed: Oct. 5, 2009

(51) Int. Cl.
 *A61B 1/00* (2006.01)
(52) U.S. Cl. ......... 600/101; 600/117; 600/127; 600/188
(58) Field of Classification Search .................. 248/157; 362/190; 348/188; 600/101, 118, 301, 117, 600/127, 236
See application file for complete search history.

(56) References Cited

U.S. PATENT DOCUMENTS

| | | | | |
|---|---|---|---|---|
| 4,349,014 | A | * | 9/1982 | Takamatsu .................... 600/109 |
| 4,613,232 | A | * | 9/1986 | Diener et al. ................. 356/124 |
| 4,975,573 | A | * | 12/1990 | Girard ........................ 250/252.1 |
| 5,494,530 | A | * | 2/1996 | Graf ............................... 134/18 |
| 5,820,547 | A | * | 10/1998 | Strobl et al. .................... 600/127 |
| 5,923,416 | A | * | 7/1999 | Rosow et al. ............. 356/124.5 |
| 5,966,210 | A | | 10/1999 | Rosow et al. |
| 6,069,691 | A | * | 5/2000 | Rosow et al. ............. 356/124.5 |
| 6,203,492 | B1 | | 3/2001 | Davis |
| 6,498,642 | B1 | * | 12/2002 | Duckett ........................ 356/244 |
| 6,511,418 | B2 | * | 1/2003 | Shahidi et al. ................ 600/117 |
| 6,575,904 | B2 | * | 6/2003 | Nagai et al. ................... 600/301 |
| 6,673,011 | B1 | | 1/2004 | Hilger |
| 6,734,958 | B1 | * | 5/2004 | MacKinnon et al. ......... 356/236 |
| 6,793,399 | B1 | * | 9/2004 | Nguyen .......................... 385/53 |
| 6,833,912 | B2 | * | 12/2004 | Lei et al. ...................... 356/124 |
| 6,992,696 | B1 | * | 1/2006 | Albertelli ...................... 348/188 |
| 7,022,065 | B2 | * | 4/2006 | Leiner et al. .................. 600/101 |
| 7,075,636 | B2 | * | 7/2006 | MacKinnon et al. ......... 356/236 |
| 7,170,677 | B1 | * | 1/2007 | Bendall et al. ................ 359/464 |
| 7,304,663 | B2 | * | 12/2007 | Albertelli ...................... 348/188 |

(Continued)

OTHER PUBLICATIONS

Rasool Khadem et al., Endoscope Calibration and Accuracy Testing for 3D/2D Image Registration, CBYON, Image Guidance Laboratories, Stanford, CA, 2001.*

(Continued)

*Primary Examiner* — Clayton E Laballe
*Assistant Examiner* — Kevin Butler
(74) *Attorney, Agent, or Firm* — C. Brandon Browning; Maynard Cooper & Gale, PC

(57) ABSTRACT

The invention relates to test equipment for rigid endoscopes, but also for flexible endoscopes and video endoscopes. The equipment includes an enclosure having a cover hingedly coupled to a base, an optical test target coupled to the cover, an endoscope support stand pivotably coupled to the enclosure and a bed contained within the base including a plurality of indentations shaped for receiving individual pieces of endoscope testing equipment. The testing equipment can include magnification loupes, light post adapters, battery powered light sources, cleansing tissues and a ruler. A support bracket is coupled between the cover and the endoscope support stand wherein the endoscope support stand is pivotably coupled to the support bracket.

17 Claims, 5 Drawing Sheets

U.S. PATENT DOCUMENTS

| | | | | |
|---|---|---|---|---|
| 7,340,943 | B2* | 3/2008 | Jackson et al. | 73/49.2 |
| 7,564,626 | B2* | 7/2009 | Bendall et al. | 359/462 |
| 7,586,521 | B2* | 9/2009 | Wong | 348/222.1 |
| 8,040,496 | B2* | 10/2011 | Leiner et al. | 356/73.1 |
| 8,139,117 | B2* | 3/2012 | Dwinell et al. | 348/188 |
| 8,172,077 | B1* | 5/2012 | Gray | 206/45.24 |
| 2001/0051761 | A1* | 12/2001 | Khadem | 600/117 |
| 2002/0010384 | A1* | 1/2002 | Shahidi et al. | 600/118 |
| 2003/0100818 | A1* | 5/2003 | Lei et al. | 600/117 |
| 2004/0227935 | A1* | 11/2004 | MacKinnon et al. | 356/236 |
| 2005/0049457 | A1* | 3/2005 | Leiner et al. | 600/117 |
| 2005/0200842 | A1* | 9/2005 | Bonningue et al. | 356/241.1 |
| 2006/0252990 | A1* | 11/2006 | Kubach | 600/118 |
| 2007/0060791 | A1* | 3/2007 | Kubach | 600/117 |
| 2007/0238923 | A1* | 10/2007 | Kubach | 600/118 |
| 2007/0251037 | A1* | 11/2007 | Maguire et al. | 15/104.001 |
| 2008/0228031 | A1* | 9/2008 | Leiner et al. | 600/109 |
| 2009/0259102 | A1* | 10/2009 | Koninckx et al. | 600/111 |
| 2009/0284963 | A1* | 11/2009 | Intravatola | 362/190 |
| 2011/0140003 | A1* | 6/2011 | Beck et al. | 250/459.1 |
| 2011/0149057 | A1* | 6/2011 | Beck et al. | 348/65 |

OTHER PUBLICATIONS

Shahidi et al., "Implemenation, Calibration and Accuracy Testing of an Image-Enhanced Endoscopy System", IEEE 2002.*

IMS, "Rigid Endoscope Repair Technical Excellence", http://www.imsready.com/articles/article_faq_rigid_01.aspx#turntime , © 2012 Integrated Medical Systems International, Inc. All rights reserved.*

Lighthouse Imaging "EndoLume", http://www.lighthouseoptics.com/medical-optics-products/endoscopic-measurement-instruments, Portland, ME, © Copyright 2012 | Lighthouse Imaging Corporation | All Rights Reserved.*

Lighthouse Imaging "EndoBench XT ENdoscope Quality Tester—Measurement Instrumentation"; © Copyright 2012 | Lighthouse Imaging Corporation | All Rights Reserved, Portland, ME, © Copyright 2012 | Lighthouse Imaging Corporation | All Rights Reserved.*

Wikipedia The Free Encyclopedia, "Optical Resolution"; Wikimedia Foundation, Inc., a non-profit organization.*

BC Group International Inc.; BC 10-12500; Endocopy System Testing Kit, St. Louis, MO, Jan. 5, 2007.*

* cited by examiner

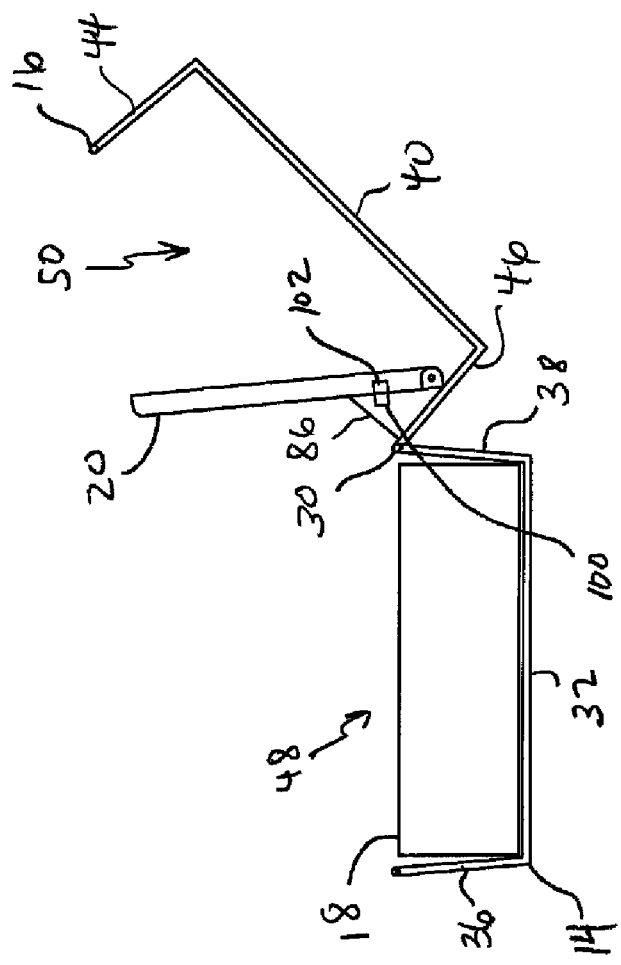
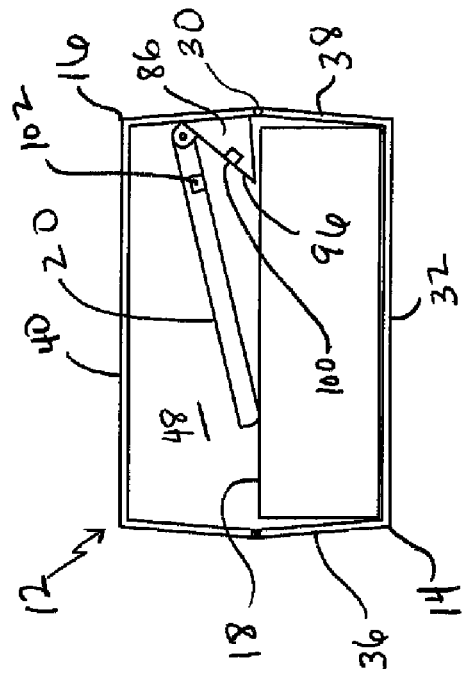
FIG. 4
FIG. 3

ENDOSCOPE TESTING DEVICE AND METHOD OF USING SAME

FIELD OF THE INVENTION

The present invention is directed to device for testing optical equipment, and more particularly, to a portable testing kit and method of using same for testing the optical system and the illumination system of an endoscope.

BACKGROUND OF THE INVENTION

Technical and medical endoscopes are delicate optical instruments that are introduced into technical and human cavities to inspect the interiors thereof. Such endoscopes can be rigid endoscopes containing a lens system, flexible endoscopes containing a flexible image guiding bundle or video endoscopes. Typically, endoscopes contain an outer tube and an inner tube. The space between the outer tube and the inner tube is filled with illumination fibers which guide externally created light inside of the cavities. Within the inner tube of rigid endoscopes there is provided an optical system which relays an image of the cavity from the distal tip of the endoscope back to the proximal end of the endoscope. This relayed image can be observed at the proximal end by the operator's eye or captured by a video camera. Rigid endoscopes are inserted along an insertion tube which cannot freely move in the body cavity. Thus, to look at a direction sideward to the insertion direction rigid endoscopes often have a deflecting prism at the distal tip of the optical system. For flexible endoscopes, the cavity image is relayed by a fiber image bundle to the ocular at the proximal end of the endoscope. Video endoscopes have a chip built into the distal tip of the endoscope that delivers the cavity image in electronic form directly to an external video controller.

Because of the extreme physical dimensions of endoscopes, endoscopes are often stressed during cleaning, sterilization and usage. These stresses can bend the endoscopes or break, chip or dislocate the glass lenses and deflection prisms. Further, the illumination fibers can break, and debris can accumulate on the ends of the fiber illumination bundle or on the windows enclosing the optical system. Also, fluid can enter into the optical system of the instruments during cleaning or sterilization. Accordingly, endoscopes can be damaged or their performance degraded to an extent where the safe usage of the instruments is no longer warranted.

When endoscopes are damaged, they must be separated from the inventory and properly cleaned or sent out to a service company for internal cleaning or repair. If the damage is not detected prior to the planned surgery the medical procedure can be delayed, cancelled or the outcome of the procedure can be compromised.

In the patent literature various test equipment for endoscopes is described. U.S. Pat. Nos. 6,203,492 and 6,673,011 describe testing devices that hold and protect endoscopes when the pupil of the endoscopes are scanned for damage and debris. These testing devices are easy to use but do not give a clear determination if the equipment is ready for use or not. The testing devices described in U.S. Pat. Nos. 4,613,232; 5,966,210 and 6,498,642 use time consuming procedures to collect data and require technical knowledge and skills to operate. Further, the data have then to be checked against the manufacturer's specifications and tolerances. U.S. Pat. Nos. 6,069,691 and 7,022,065 describe testing devices for endoscopes which are automated or computer controlled. These devices are less complicated to operate, but they are expensive and delicate.

SUMMARY OF THE INVENTION

The present invention is directed to a portable, endoscope testing device that can be used by non-technical staff to determine if an endoscope is ready for use in surgery. The device can be used to quickly determine the basic functionality of an endoscope prior to submitting it to the operating room. According to one aspect of the invention, there is provided an endoscope testing kit including an enclosure having a cover hingedly coupled to a base, an optical test target coupled to the cover, an endoscope support stand pivotably coupled to the enclosure, and a bed contained within the base including a plurality of indentations shaped for receiving individual pieces of endoscope testing equipment. The testing equipment can include magnification loupes, light post adapters, battery powered light sources, cleansing tissues and a ruler. Preferably, a support bracket is coupled between the cover and the endoscope support stand wherein the endoscope support stand is pivotably coupled to the support bracket. Further, a pair of opposing magnets can be coupled to the endoscope support stand and the support bracket and arranged to selectively connect and disconnect to one another when the cover is open and closed.

According to a second aspect of the invention, there is provided a method of testing an endoscope. The method includes pivoting a cover of an enclosure into an open position, pivoting an endoscope support stand coupled to the cover into a testing position, supporting the endoscope on the endoscope support stand, and viewing an optical test target coupled to the cover through the endoscope. The method also includes removing one or more endoscope testing devices from a base of the enclosure and testing the endoscope with the testing devices, the testing device being selected from high magnification loupes, low magnification loupes, battery powered light sources, and a rigid member having a straight edge.

According to another aspect of the invention, there is provided a method of making an endoscope testing device. The method includes coupling a cover to a base thereby forming an enclosure, coupling an optical test target to an interior surface of the cover, coupling an endoscope support stand to the enclosure, and supporting a plurality of endoscope testing devices within the base. Further, a white layer or sheet can be coupled to the interior surface of the cover. Preferably, the endoscope support stand is pivotably coupled to the interior surface of the cover using a bracket and a pair of magnets. In this way, the endoscope support stand can be oriented substantially upright in a testing position when the cover is open and substantially horizontal when the cover is closed.

BRIEF DESCRIPTION OF THE DRAWINGS

FIG. 3 is a sectional view of the testing device of FIG. 1 in a closed position.

FIG. 4 is a sectional view of the testing device of FIG. 1 in an open position.

DETAILED DESCRIPTION OF PRESENTLY PREFERRED EMBODIMENTS

Figure 1:
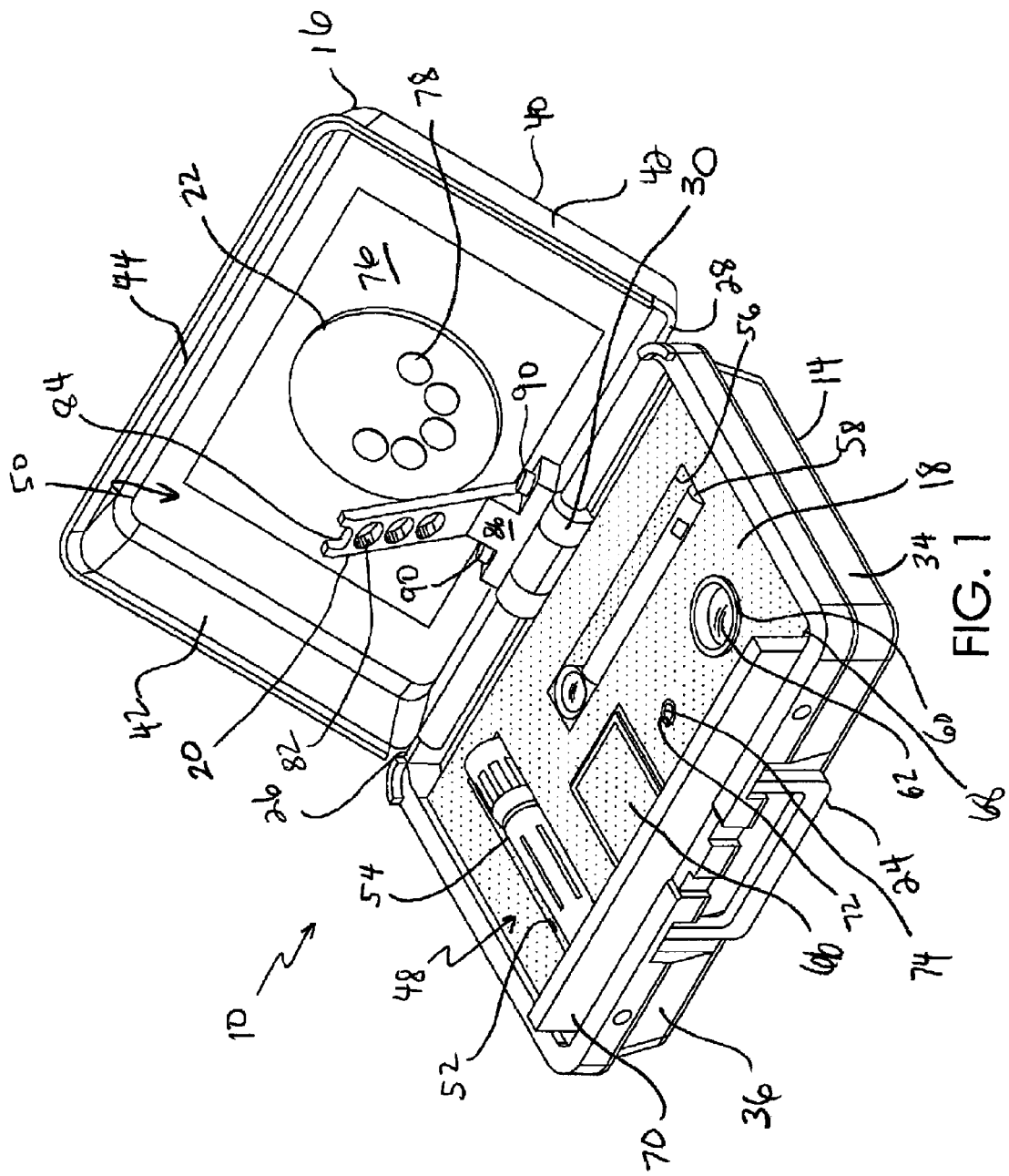
FIG. 1 is a perspective view of a portable endoscope testing device in accordance with a preferred embodiment of the present invention.
Figure 2:
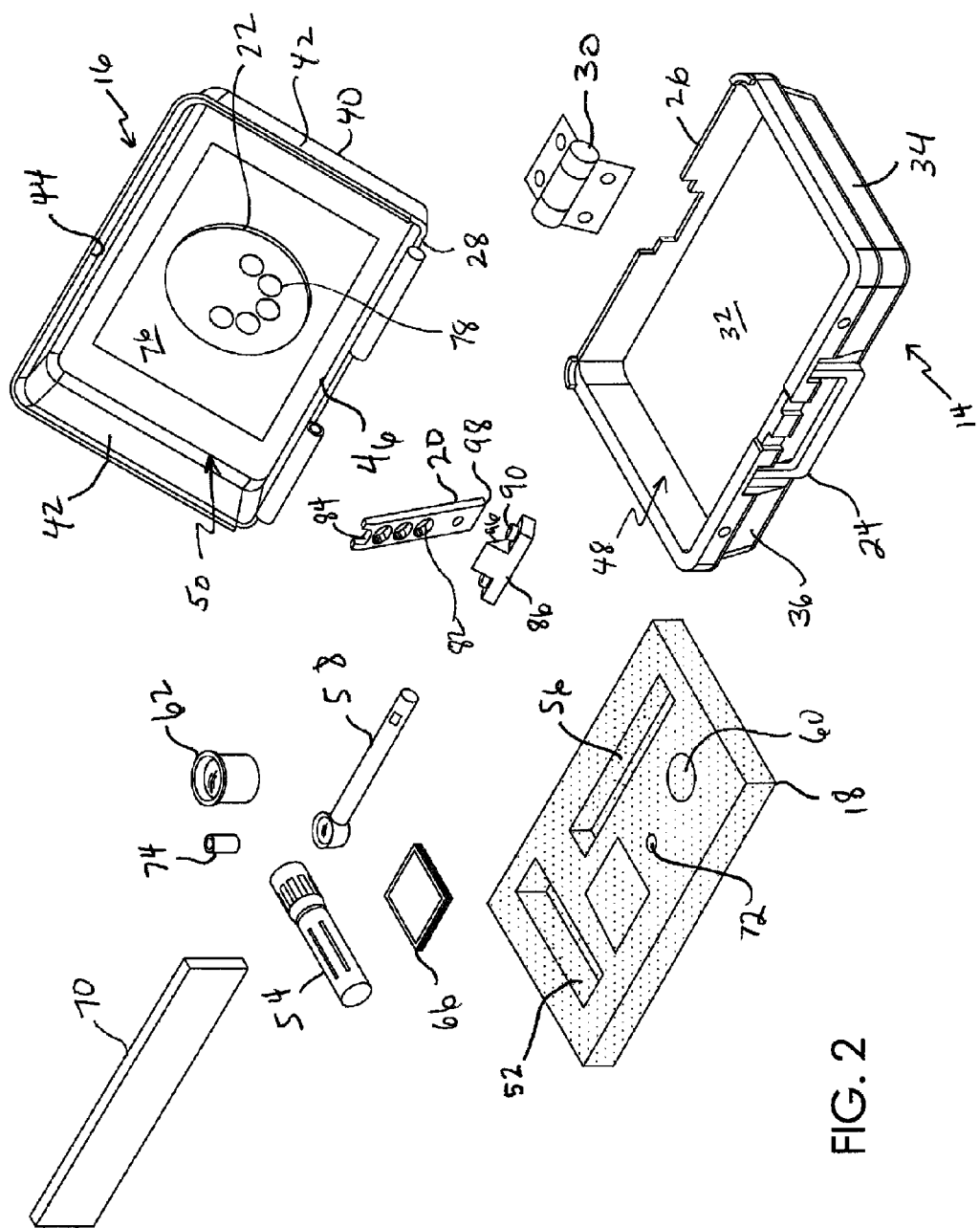
FIG. 2 is an exploded view of the testing device of FIG. 1.
Figure 5:
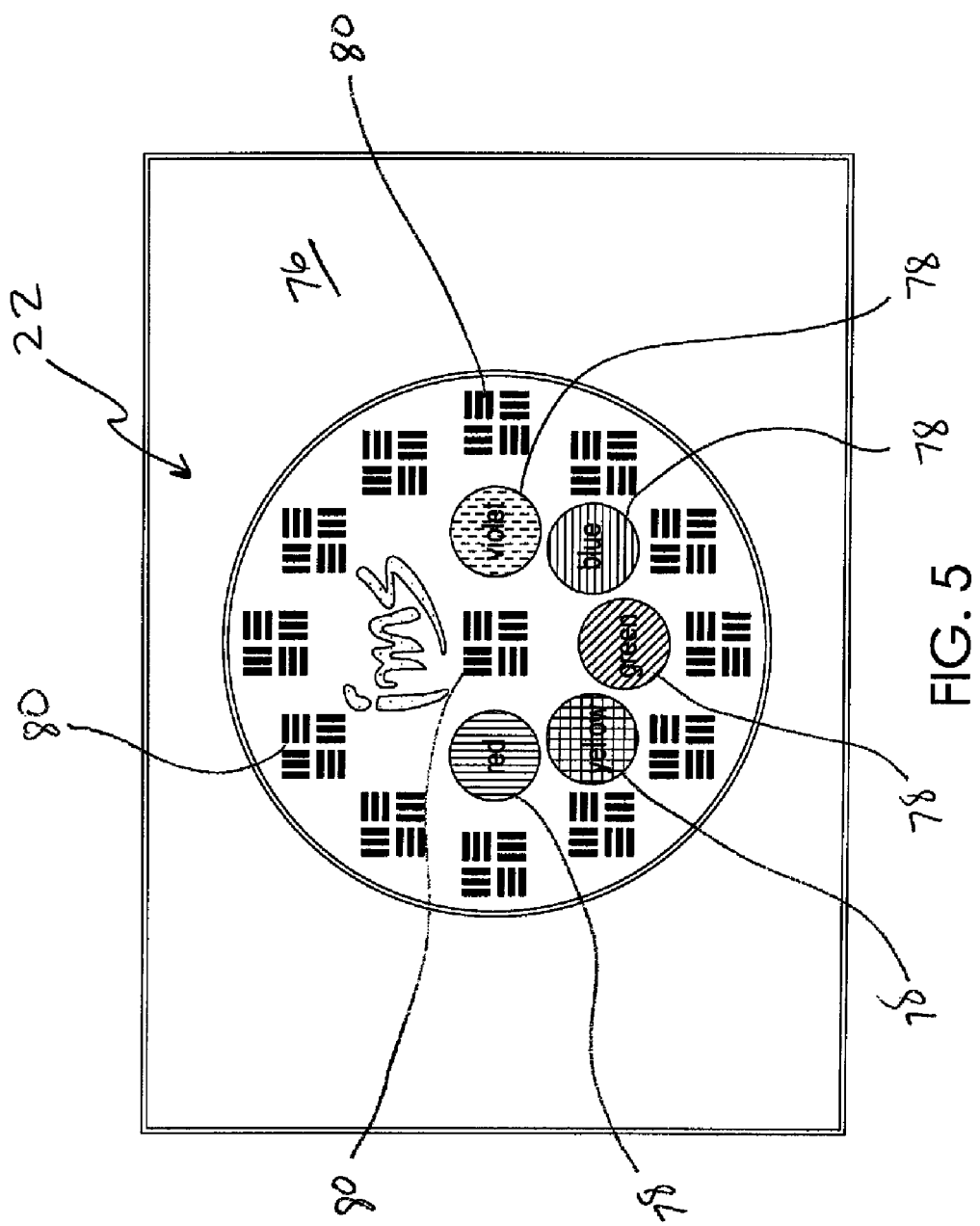
FIG. 5 is a top plan view of the an optical test target of the testing device of FIG. 1.
Figure 6:
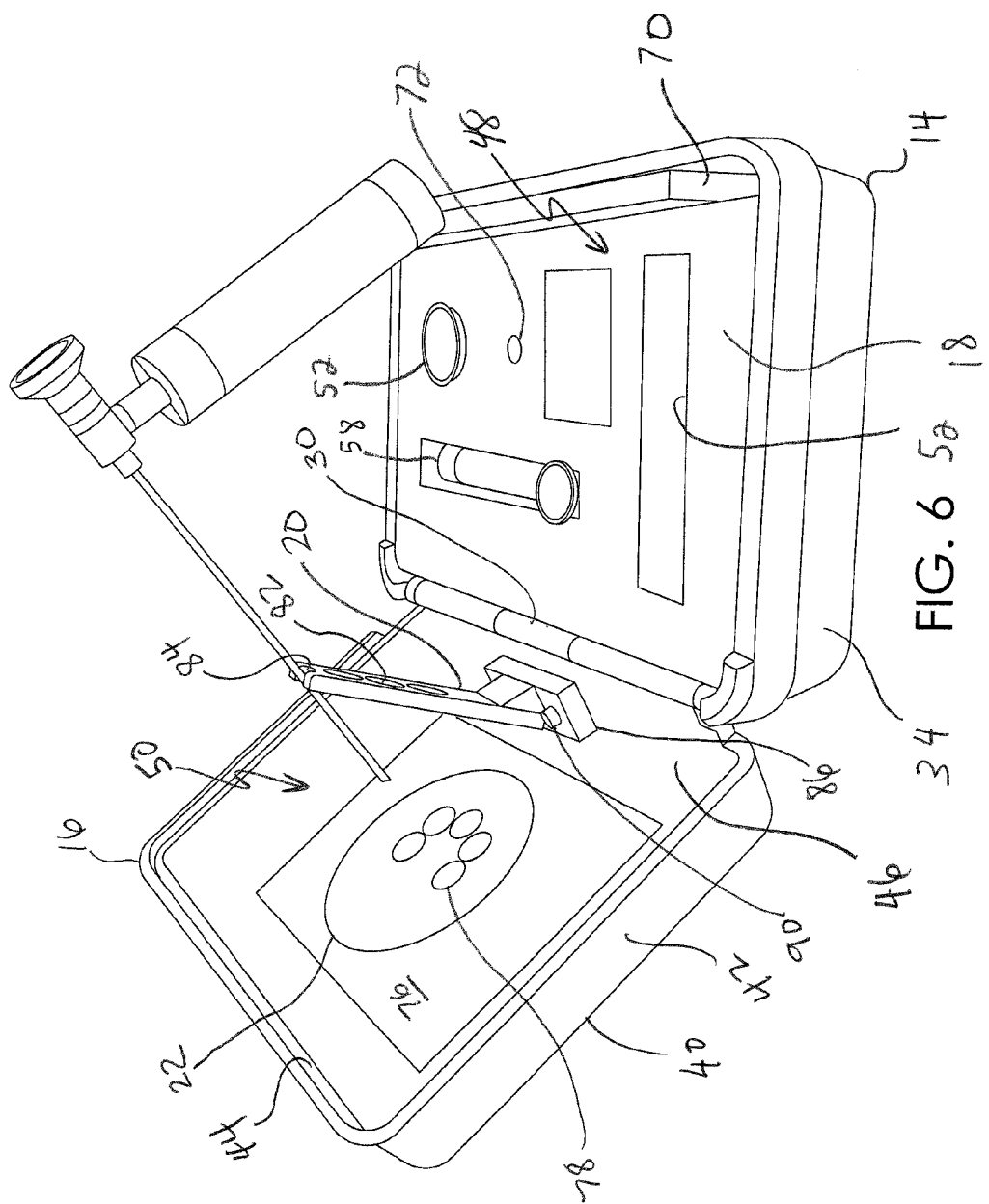
FIG. 6 is a perspective view of the testing device of FIG. 1 and an endoscope supported by the device during testing.

FIGS. 1 through 6 display a portable endoscope testing device 10 in accordance with a preferred embodiment of the present invention. Referring to FIGS. 1 and 2, testing device 10 generally includes a case or enclosure 12 composed of a base 14 and a cover 16. Base 16 is provided for securely accommodating a variety of endoscope testing devices within a foam bed 18 held within the base. Cover 16 is provided for supporting a monopod or endoscope support stand 20 and an optical test target 22 that is aligned with stand 20. As described in more detail below, enclosure 12 is maintained in a closed position when device 10 is in storage, not in use or during transportation of the device. Alternatively, when testing device 10 is to be used to test an endoscope, enclosure 12 is oriented into an open position thus exposing the variety of endoscope testing devices and maneuvering support stand 20 into a testing position.

More particularly, enclosure 12 is provided in the form a small, durable carrying case capable of containing the endoscope testing devices and support stand 20. Base 14 of enclosure 12 is composed of a floor 32, opposing lateral walls 34, a front wall 36 and a back wall 38 which together define a base interior space 48. Similarly, cover 16 is composed of a top wall 40, opposing lateral walls 42, a front wall 44 and a back wall 46 which together define a cover interior space 50. Base 14 is pivotably coupled along an upper edge 26 of back wall 36 thereof to a lower, rear edge 28 of back wall 46 of cover 16. A friction hinge 30 is provided there between to allow cover 16 to be maintained in an open portion and at a desired angle relative to base 14 during endoscope testing. A handle 24 coupled to front wall 36 of base 14 allows for ease of carrying enclosure 12 during transportation.

Contained within base interior space 48 is foam bed 18. Bed 18 is secured therein by an adhesive applied between floor 32 and the bottom side of bed 18 and extends completely between opposing lateral walls 34, front wall 36 and back wall 38 of base 14. Formed within foam bed 18 are a number of cut-outs or indentations configured to securing and snugly receiving individual endoscope testing devices. These indentations include a first indentation 52 configured for receiving a battery powered, hand-held, variable output LED light source 54 which can be connected to the light post of an endoscope, a second indentation 56 for receiving an illuminated high magnification loupe 58 for inspecting the distal tip of the endoscope and the distal tip of an endoscope fiber illumination bundle, a third indentation 60 for receiving a low magnification loupe 62 for inspecting the area of the endoscope exit pupil, a fourth indentation for receiving a package of cleansing tissues 66, a fifth indentation 68 for receiving a ruler 70 for testing the straightness of endoscope shafts and a sixth indentation 72 for receiving a light post adapter 74 for different adapter standards. The indentations can be arranged within foam bed 18 in any manner so long as the endoscope test devices contained therein are individually and securely confined within bed 18. Alternatively, ruler 70 may be arranged directly against the interior portion of front wall 36 of base 14. In this arrangement, foam bed 18 does not fully extend between front wall 36 and back wall 38 of base 14 and no indentation is provided in bed 18 for the ruler. Also, ruler 70 can be fixed to front wall 36 of base 14 using screws and the like.

Contained within cover interior space are optical test target 22 and endoscope support stand 20. Test target 22 is a round member centered on the interior side of top wall 40 on a white, rectangular background 76 adhered to top wall 40. The test target includes a number of differently colored circles 78 namely, a red circle, a yellow circle, a green circle, a blue circle and a purple circle. Test target 22 also includes several groupings of vertically and horizontally arranged rows and columns of lines or resolution patterns 80. Optical test target 22 is used to evaluate the image quality of an endoscope and the white background 76 is used to evaluate the evenness of the illumination and as background for the check of the exit pupil area of the endoscope. Endoscope support stand 20 comprises a flat, elongate rectangular structure having a numbed of openings 82 there through for supporting an endoscope and that open substantially toward test target 22 when enclosure 12 is on an open position. Stand 20 also includes a concave upper edge 84 for receiving an endoscope during testing. A bracket 86 is used to pivotably couple support stand 20 to the interior surface of back wall 46 of cover 16.

More particularly, bracket 86 is centrally arranged on the interior surface of back wall 46 so that it is aligned with test target 22 and divides test target 22 into two equal halves. Bracket 86 includes a substantially flat backside coupled directly to back wall 46 using a pair of screws 90 inserted into an pair openings positioned along the lateral portions of the bracket. Centrally located on bracket 86 opposite its backside is a raised, angled portion 96 having a triangle shaped cross-section. Support stand 20 is pivotably coupled at its bottom end 98 thereof to angled portion 96 and arranged to lie directly against angled portion 96 when enclosure 12 is in an open position. To maintain support stand 20 in an upright position and pressed against angled portion 96 when enclosure 12 is in an open position, angled portion 96 includes a first magnet 100 which is directly aligned with a second magnet 102 embedded in support stand 20. The attraction of magnets 10, 102 to one another, detachably adheres support stand 20 to angled portion 96 when desired thus holding support stand 20 is a desired position.

FIG. 3 depicts enclosure 12 with cover 16 in the closed position. In this position, endoscope support stand 20 is pivoted away from angled portion 96 and oriented substantially horizontally within enclosure 12. Further, magnets 100, 102 are separated. This occurs when cover 16 is pivoted towards base 14 and upper edge 84 of support stand contacts foam bed 18. As cover 16 is closed further, upper edge 84 of support stand 20 slides along bed 18 and is thereby forced away from angled portion 96 thus overcoming the attractive force of magnets 100, 102. Accordingly, the force of closing cover 16 detaches support stand 20 from angled portion 96.

FIG. 4 depicts enclosure 12 with cover 16 in the open position. In this position, support stand 20 is pressed against angled portion 96 by the attraction of magnets 100, 102 to one another. Angled portion 96 and support stand 20 are brought together by gravity when cover 16 is pivoted open and away from base 14. Once magnets 100, 102 couple to one another, stand 20 remains attached to angled portion 96 until cover 16 is again closed.

Testing device 10 can be used by trained non technical staff to determine if an endo scope is ready for use in surgery, if its functionality can be restored on site and if the endoscope needs to be send out to a specialized repair facility for cleaning or repair. Such determinations are made by subjecting the endoscopes to one or more of the following physical and optical testing procedures using device 10.

Testing Procedures

With cover 16 in the open position, ruler 70 can be used to check the straightness of the outer tube of an endoscope by holding the outer tube against ruler 70 as ruler 70 remains connected to base 14 and turning the endoscope tube one full turn. A bent outer tube indicates the endoscope has undergone a mechanical stress which can damage or dislocate optical components within the endoscope. That said, even if the tube itself is straight, the tube can be bent at the connection to the endoscope body. This can be checked by pressing an axial surface of the endoscope body against one side of ruler 70.

After cleaning the outside surface of the windows on the distal and proximal end of the endoscope optical system the condition of these windows can be checked with high magnification loupe 58 with built in illumination. Any remaining deposited debris is removed if possible. Sharp edges, cracks or evidence of internal fluid under the windows can be observed using loupe 58 which indicates a damaged distal tip of the endoscope. After cleaning the entrance and exit surface of the fiber illumination bundle these surfaces can also be checked with high magnification loupe 58 with built in illumination for any remaining debris.

The illumination fibers built in the endoscope do not change the internal transmission or experience any color degradation over time. However, some of the fibers can break or the fiber ends can be chipped or deposits on the fibers can reduce the light output so that the endoscope cannot transmit enough light to sufficiently illuminate the body cavity. To check the condition of the illumination fiber bundle, battery powered handheld LED light source 54 needs to be connected to the light post of the endoscope. Handheld LED light source 54 also needs to be set to a low light output. When handheld LED light source 54 is attached to the fiber illumination bundle at the light post of the endoscope, the fiber bundle at the distal tip can be visually checked with high magnification loupe 58 for any broken or chipped fibers. Also any deposits on the fiber bundle end can be detected.

LED light source 54 can be connected to the light post of an endoscope directly or through a light post adapter 74. Preferably, battery powered handheld light source 54 has a low light position and one or two high power output positions. The low light position is used to illuminate the fiber illumination bundle so that the output surface at the endoscope distal tip can be inspected with high magnification loupe 58. The high power light output can be used to illuminate the object field of large and small endoscopes during the inspection of the optical target. Alternatively, the light out put can be continuous from low to high light output. Light post adapter 74 is used to connect the battery powered handheld LED light source 54 to endoscopes of different manufacturers.

If none of these inspections indicates a damaged endoscope, the still connected handheld LED light source 54 is switched to high power light output. The endoscope is then placed on concave upper edge 84 of support stand 20, and the distal tip of the endoscope is oriented toward optical test target 22. Thereafter, the angle of cover 16 of enclosure 12 is adjusted relative to base 14, and the endoscope is tilted and moved along the shaft axis until optical test target 22 is centered in the field of view of the endoscope and test target 22 fills the circular image field of the endoscope. By comparing resolution pattern 80 of the center of the image field with resolution patterns 80 distributed around the periphery of test target 22 the image quality over the whole image field can be evaluated. This procedure is a functional test which indicates if the image of the endoscope delivers a sharp crisp image of an object positioned at an average working distance of the tested endoscope. The evenness of the illumination in the object field of the endoscope can also be evaluated by looking through the ocular of the endoscope. The best way to evaluate the evenness of the illumination is to turn the scope slightly until the object field covers only white background 76 surrounding optical target 22.

After the optical system of the endoscope is evaluated, the clear aperture of the optical train of the endoscope is inspected. It is usual to scan the pupil area of optical systems to detect any dust, debris, fluid or damaged optical components. To inspect the pupil area over a certain depth range, the endoscope stays connected to handheld LED light source 54, and the endoscope remains supported on upper edge 84 of support stand 20 facing the white background 76 surrounding optical target 22. Thereafter, low magnification loupe 62 is moved along the optical axis behind the end of the eyepiece of the endoscope. By looking through low magnification loupe 62 said loupe is moved along the optical axis of the eyepiece of the endoscope, until the pupil area is scanned for dust, debris, fluid or damaged optical components.

As will be apparent to one skilled in the art, various modifications can be made within the scope of the aforesaid description. Such modifications being within the ability of one skilled in the art form a part of the present invention and are embraced by the claims below.

It is claimed:

1. An endoscope testing kit comprising,
   an enclosure including a cover hingedly coupled to a base,
   an optical test target coupled to the cover,
   a white background coupled to an interior surface of the cover about the optical test target,
   an endoscope support stand pivotably coupled to the enclosure, and
   a bed contained within the base including a plurality of indentations shaped for receiving individual pieces of endoscope testing equipment.

2. The kit according to claim 1 wherein the plurality of indentations include a first indentation shaped to snugly receive a magnification loupe, a second indentation shaped to snugly receive a light post adapter and a third indentation shaped to snugly receive a battery powered light source.

3. The kit according to claim 1 including a support bracket coupled between the cover and the endoscope support stand wherein the endoscope support stand is pivotably coupled to the support bracket.

4. An endoscope testing kit comprising,
   an enclosure including a cover hingedly coupled to a base,
   an optical test target coupled to the cover,
   an endoscope support stand pivotably coupled to the enclosure, and
   a bed contained within the base including a plurality of indentations shaped for receiving individual pieces of endoscope testing equipment,
   wherein the plurality of indentations include a first indentation shaped to snugly receive a magnification loupe, a second indentation shaped to snugly receive a light post adapter and a third indentation shaped to snugly receive a battery powered light source, and
   wherein the plurality of indentations include a fourth indentation shaped to snugly receive a package of cleansing tissues and a fifth indentation shaped to snugly receive an elongate, rectangular member.

5. The kit according to claim 1 wherein the base contains a high magnification loupe, a low magnification loupe, a light post adapter and a battery powered light source.

6. An endoscope testing kit comprising,
   an enclosure including a cover hingedly coupled to a base, wherein the base contains a high magnification loupe, a low magnification loupe, a light post adapter and a battery powered light source, an optical test target coupled to the cover,
an endoscope support stand pivotably coupled to the enclosure,
a bed contained within the base including a plurality of indentations shaped for receiving individual pieces of endoscope testing equipment,
cleansing tissues and a ruler.

7. An endoscope testing kit comprising,
an enclosure including a cover hingedly coupled to a base,
an optical test target coupled to the cover,
an endoscope support stand pivotably coupled to the enclosure, and
a bed contained within the base including a plurality of indentations shaped for receiving individual pieces of endoscope testing equipment,
a support bracket coupled between the cover and the endoscope support stand wherein the endoscope support stand is pivotably coupled to the support bracket, and
a first magnet coupled to the endoscope support stand and a second magnet coupled to the support bracket wherein the first magnet and the second magnet are arranged to selectively connect and disconnect.

8. A method of testing an endoscope comprising,
pivoting a cover of an enclosure into an open position,
pivoting an endoscope support stand coupled to the cover into a testing position,
supporting the endoscope on the endoscope support stand, and
viewing an optical test target coupled to the cover through the endoscope,
wherein pivoting the cover into an open position pivots the endoscope support stand into the testing position.

9. The method according to claim 8 including removing a plurality of endoscope testing devices from a base of the enclosure and testing the endoscope with the testing devices.

10. The method according to claim 9 wherein the plurality of endoscope testing devices include a high magnification loupe, a low magnification loupe and a battery powered light source.

11. A method of testing an endoscope comprising,
pivoting a cover of an enclosure into an open position,
pivoting an endoscope support stand coupled to the cover into a testing position,
supporting the endoscope on the endoscope support stand,
viewing an optical test target coupled to the cover through the endoscope, and
removing a plurality of endoscope testing devices from a base of the enclosure and testing the endoscope with the testing devices,
wherein the plurality of endoscope testing devices include a rigid member having a straight edge.

12. A method of making an endoscope testing device comprising,
coupling a cover to a base thereby forming an enclosure,
coupling an optical test target to an interior surface of the cover,
coupling an endoscope support stand to the enclosure,
coupling a white layer to the interior surface of the cover, and
supporting a plurality of endoscope testing devices within the base.

13. The method according to claim 12 wherein the endoscope support stand is pivotably coupled to the interior surface of the cover.

14. The method according to claim 12 further comprising coupling a bracket between the endoscope support stand and the cover.

15. The method according to claim 12 further comprising arranging the endoscope support stand to be substantially upright when the cover is open and substantially horizontal when the cover is closed.

16. The method according to claim 12 further comprising arranging an interior of the base to snuggly support one or more of the plurality of endoscope testing devices.

17. The method according to claim 12 further comprising arranging the endoscope support stand to detachably adhere to a bracket coupled to the enclosure, wherein the endoscope support stand is pivotably coupled to the bracket.

* * * * *